United States Patent [19]

Munford et al.

[11] Patent Number: 5,200,184
[45] Date of Patent: Apr. 6, 1993

[54] LIPOPOLYSACCHARIDES OF REDUCED TOXICITY AND THE PRODUCTION THEREOF

[75] Inventors: Robert S. Munford; Catherine L. Hall, both of Dallas, Tex.

[73] Assignee: Board of Regents, The University of Texas System, Austin, Tex.

[21] Appl. No.: 728,763

[22] Filed: Jul. 8, 1991

Related U.S. Application Data

[63] Continuation of Ser. No. 515,657, Apr. 24, 1990, abandoned, which is a continuation of Ser. No. 53,044, May 22, 1987, abandoned, which is a continuation-in-part of Ser. No. 868,428, May 28, 1986, Pat. No. 4,929,604.

[51] Int. Cl.$^5$ .................. A61K 37/54; A61K 31/715; C12N 9/18
[52] U.S. Cl. .................. 424/94.61; 435/187; 514/53
[58] Field of Search .................. 435/197, 84; 514/53, 514/54; 536/53; 424/94.61

[56] References Cited

U.S. PATENT DOCUMENTS

| | | | |
|---|---|---|---|
| 4,057,685 | 11/1977 | McIntire | 536/18 |
| 4,148,877 | 4/1979 | Choay et al. | 424/92 |
| 4,185,090 | 1/1980 | McIntire | 424/92 |
| 4,242,270 | 12/1980 | Ayme et al. | 260/428 |
| 4,435,386 | 3/1984 | Ribi et al. | 424/177 |
| 4,436,727 | 3/1984 | Ribi | 424/177 |
| 4,436,728 | 3/1984 | Ribi et al. | 424/177 |
| 4,505,899 | 3/1985 | Ribi et al. | 514/8 |
| 4,505,900 | 3/1985 | Ribi et al. | 514/2 |
| 4,663,306 | 5/1987 | Cantrell . | |
| 4,677,194 | 6/1987 | Hao | 530/350 |
| 4,719,202 | 1/1988 | van Boeckel et al. . | |

OTHER PUBLICATIONS

Kotani et al., (1985), *Infect. Immun.*, 49:225–237.
Tacata et al. (1985), *Infect. Immun.*, 48:219–227.
Homma et al., (1985), *J. Biochem.*, 98:395.
Galanos et al. (1984), *Eur. J. Biochem.*, 140:221–227.
Hall and Munford (1983), *Proc. Natl. Acad. Sci. U.S.A.*, 80:6671–6675.
Rosner et al. (1979), *J. Biol. Chem.*, 254:5926–5933.

Gimber and Rafter (1969), *Arch. Biochem. Biophys.*, 135:14–20.
Takayama et al., (1984), Reviews of Infect. Diseases, vol. 6, No. 4, pp. 439–443, "Separation and Characterization of Toxic and Non–Toxic Forms of Lipid A".
Munford, et al. (1986) *Science*, vol. 234, pp. 203–205, "Detoxification of Bacterial Lipopolysaccharides (Endotoxins) by a Human Neutrophil Enzyme".

(List continued on next page.)

*Primary Examiner*—Charles L. Patterson, Jr.
*Attorney, Agent, or Firm*—Arnold, White & Durkee

[57] ABSTRACT

An acyloxyacyl hydrolase from the human promyelocyte cell line HL-60 has been found to specifically hydrolyze fatty acids from their ester linkages to hydroxy groups of 3-hydroxyfatty acids, the latter being bound in turn to LPS glycosaminyl residues. The hydrolyzed fatty acids may include dodecanoic acid, tetradecanoic acid and hexadecanoic acid. This enzyme showed a molecular weight by gel exclusion chromatography between about 50,000 Daltons and about 70,000 Daltons.

Altered bacterial LPS substantially without fatty acids bound in ester linkage to hydroxy groups of 3-hydroxyfatty acids covalently linked to a glucosaminyl moiety of LPS lipid A are produced. Since the structure of the lipid A moiety is highly conserved, acyloxyacyl hydrolase may act on LPS of many different pathogenic bacteria (for example Salmonella, Escherichia, Hemophilus, and Neisseria).

Such altered bacterial LPS, having toxicity reduced more than immunostimulatory activity, may be therapeutically useful: (1) as vaccines to prevent Gram-negative bacterial diseases by inducing antibodies to LPS O-polysaccharide or R-core antigens, (2) as antidotes to treat or prevent Gram-negative bacterial sepsis ("septic shock"), or (3) as adjuvants to enhance formation of antibodies to other antigens. The acyloxyacyl hydrolase itself may be prophylactically or therapeutically useful to detoxify endogenous LPS in patients with Gram-negative bacterial diseases. The enzyme may also be used to remove toxic LPS from therapeutic injectants.

6 Claims, 3 Drawing Sheets

OTHER PUBLICATIONS

Munford, et al. (1989), *J. Biol. Chem.*, vol. 264, No. 26, Sep. 15, 1989, "Purification of Acyloxyacyl Hydrolase, a Leukocyte Enzyme That Removes Secondary Acyl Chains from Bacterial Lipopolysaccharides", pp. 15613–15619.

Munford, R. S. (1987), J. Cell Biochem. Suppl., vol 0, No. 11, Part B, p. 106, Symposium on Bacteria: Host Cell Interaction Held at the 16th Annual UCLA Meeting on Molecular and Cellular Biology, Los Angeles, Calif., USA, Feb. 13–19, 1987, "Deacylation of Bacterial Lipopolysacchardies by Neutrophils".

Munford et al., (1986), EOS-Riv. Immunol. Immunofarmacol., vol. 6, (3, Suppl.), pp. 71–72, "Deacylation of Lipopolysaccharides by Neutrophils and Macrophases: Ayloxyacyl Hydrolysis Modifies the Bioactivities of Endotoxin".

Munford et al., (1986), 15-Immunochemistry, 105:207446q, "Deacylation of Lipopolysacchardes by Neutrophils and Macorphages: Acyloxyacyl Hydrolysis Modifies the Bioactivities of Endotoxin".

Munford and Hall (1985), *Infect. Immun.*, 48:464–473.

Vernet (1984), *Rev. Inf. Dis.*, 6:452–454.

Freudenberg et al. (1984), *Rev. Inf. Dis.*, 6:483–487.

Kotani et al. (1984), *Infect. Immun.*, 485:293–296.

Sutherland (1977), "Surface Carbohydrates of the Prokaryotic Cell", pp. 236–239.

Dialog and Lexpat Search of the Scientific and Patent Literature.

Optimal Induction of Tumor Necrosis Factor Production in Human Monocytes Requires Complete S-Form Lipopolysaccharide, vol. 57, No. 7, pp. 1953–1958.

LIPOPOLYSACCHARIDES OF REDUCED TOXICITY AND THE PRODUCTION THEREOF

The U.S. Government may have rights in the present invention because the development was partially supported by NIH grant R01 AI18188 from the Department of Health and Human Services.

This is a continuation of co-pending application Ser. No. 07/515,657, filed on Apr. 24, 1990, now abandoned, which in turn is a continuation of U.S. Ser. No. 07/053,044, filed May 22, 1987, now abandoned, which is a continuation-in-part of U.S. Ser. No. 06/868,428, filed May 28, 1981, now U.S. Pat. No. 4,929,604.

BACKGROUND OF THE INVENTION

The present invention relates to the detoxification of bacterial endotoxin (lipopolysaccharide) by enzymatic modification of its lipid A moiety. The prophylactic and therapeutic use of such detoxified endotoxins is also a subject of the present invention.

Animals mount a complex array of inflammatory responses to tissue invasion by Gram-negative bacteria. Many of these responses appear to be provoked by the lipopolysaccharides (LPS) that are present in the bacterial outer membrane. Much evidence suggests that the lipid A region of LPS directly stimulates host cells such as macrophages, neutrophils, and endothelial cells, which then mediate the inflammatory changes. Responses to LPS may be toxic (hypotension, coagulation disturbances, death) or beneficial to the infected host (enhancement of antibody formation, mobilization of phagocytes, acute phase protein synthesis, others).

Figure 1:
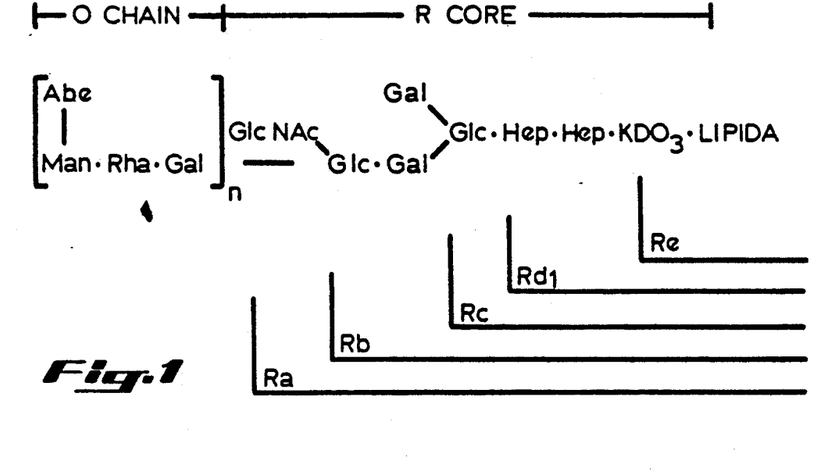
FIG. 1 shows the general structure of *Salmonella* LPS. The O-polysaccharide is connected to lipid A by the R-core region. n=0 to 50+. The structures of several R-core LPS are indicated.
Figure 2:
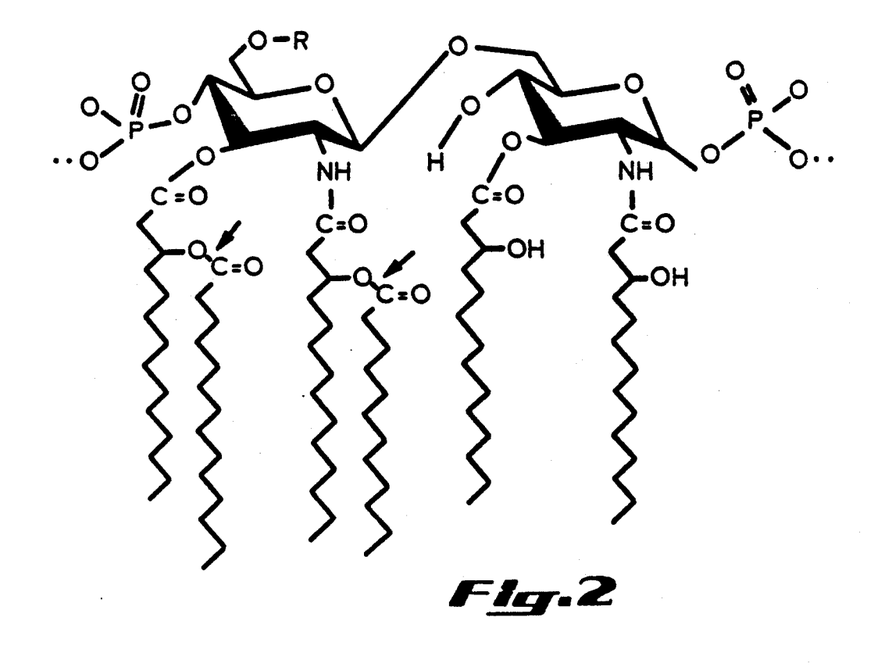
FIG. 2 shows the proposed general structure of enterobacterial lipid A. R=site of attachment of the polysaccharide chain. Arrows indicate the site of action of acyloxyacyl hydrolase.

Typical Gram-negative bacterial lipopolysaccharides (LPS) have 3 major structural regions: the O polysaccharide, the R-core oligosaccharide, and lipid A (FIG. 1 and FIG. 2). The structure of the O polysaccharide is highly variable between organisms, even in the same species, and its antigenicity serves as a basis for serotyping the bacteria. The R region is a bridge between the O-antigen and lipid A; its structure is similar in most Gram-negative bacteria. Antibodies to LPS (typically directed to O- or R-core antigenic sites) may promote phagocytosis or killing of the bacteria, or they may enhance removal of LPS from the bloodstream into sites (liver, spleen) where the LPS are degraded. The O-antigen is the most antigenic component of the LPS, yet it has little known toxicity. Lipid A, in contrast, is poorly antigenic but contains the toxic center of the molecule. The lipid A moiety is remarkably similar in structure across a wide range of bacterial genera.

The lipid A of enteric bacteria (e.g. *Salmonella, E. coli*) is a glucosamine disaccharide that is phosphorylated at positions 1 and 4' and has 6 or 7 covalently-linked fatty acids (FIG. 1). Four molecules of 3-hydroxytetradecanoate (3-OH-14:0) are attached to the glucosamine disaccharide at positions 2, 3, 2', and 3'; the hydroxyl groups of the 3-OH-14:0 residues at positions 2' and 3' (and sometimes 2) are substituted with normal fatty acids (dodecanoate, tetradecanoate, hexadecanoate) to form acyloxyacyl groups. In 1983 the discovery of a novel enzymatic activity was reported. This enzyme was an acyloxyacyl hydrolase, found in the granule fraction of human peripheral blood neutrophils, that selectively removed the nonhydroxylated acyl chains from *Salmonella typhimurium* LPS (Hall and Munford (1983) Proc. Nat. Acad. Sci. V 80, pp 6671–6675). It was known that *Dictyostelium discoideum* (slime mold), which utilizes Gram-negative bacteria as a major foodstuff, contains enzymes that remove nonhydroxylated and hydroxylated acyl chains from LPS (Rosner et al. (1979) J. Biol. Chem. V 254, pp 5926–5933). The experiments of Gimber and Rafter (Arch. Biochem. Biophys, (1969), V 135, pp 14–20) had also suggested that deacylation of LPS is carried out by intact neutrophils.

Recent studies of the biological activities of chemically synthesized lipid A analogs and biosynthetic precursors of lipid A have provided valuable information about structure-activity relationships (Galanos et al. (1984) Eur. J. Biochem. V 140, p 221; Takada et al. (1985) Infect. & Immun. V 48, p 219; Kotani et al. (1985) Infect. Immun. V 49, p 225; and Homma et al. (1985) J. Biochem. V 98, p 395). Lipid A analogs that lack nonhydroxylated acyl chains are not reactive in the dermal Shwartzman test and have reduced pyrogenicity, yet they are nearly equipotent with complete lipid A in various assays of immune stimulation such as B-cell mitogenicity, adjuvanticity, and stimulation of macrophages to release $PGE_2$. The effects of acyloxyacyl hydrolase on the biological activities of LPS are in general agreement with these earlier findings: acyloxyacyl hydrolysis detoxifies LPS without destroying the immunostimulatory activity.

SUMMARY OF THE INVENTION

An acyloxyacyl hydrolase from human neutrophils has been found to specifically hydrolyze fatty acids from their ester linkages to hydroxy groups of 3-hydroxyfatty acids, the latter being bound in turn through their carboxylate functions to LPS glucosaminyl residues. The hydrolyzed fatty acids may include, for example, dodecanoic acid, tetradecanoic acid and hexadecanoic acid. This enzyme, at least partially purified from human promyelocytes, has the above described specificity. Gel chromatography of the purified enzyme preparation showed a molecular weight between about 50,000 Daltons and about 70,000 Daltons. Analysis of the enzyme by electrophoresis in 11% polyacrylamide gels in the presence of sodium dodecyl sulfate showed an apparent molecular weight of 70,000 to 75,000 Daltons.

Altered bacterial LPS substantially without fatty acids bound in ester linkage to hydroxy groups of 3-hydroxyfatty acids covalently linked to a glucosaminyl moiety of LPS lipid A are produced as described herein. Said altered bacterial LPS characteristically have bound 3-hydroxyfatty acids with hydroxy functions at least substantially unesterified. Since the structure of the lipid A moiety is highly conserved, acyloxyacyl hydrolase may act on LPS of many different pathogenic bacteria (those studied include *Salmonella, Escherichia, Hemophilus,* and *Neisseria*).

Such altered bacterial LPS, having toxicity reduced more than immunostimulatory activity, may be therapeutically useful. Such therapeutic usefulness comprises use of the altered LPS (1) as vaccines to prevent Gram-negative bacterial diseases by inducing antibodies to O-polysaccharide or R-core antigens, (2) as antidotes to treat or prevent Gram-negative bacterial sepsis ("septic shock"), or (3) as adjuvants to enhance formation of antibodies to other antigens. The acyloxyacyl hydrolase itself may be therapeutically or prophylactically useful to detoxify endogenous LPS in patients with, or at risk of, Gram-negative bacterial diseases.

BRIEF DESCRIPTION OF THE DRAWINGS

LPS is a glycolipid that has a saccharide chain covalently attached to a lipid (lipid A). LPS molecules may have different lengths of saccharide chain. The saccharide chain has two regions, O-antigen and R-core as shown. Molecules that contain both O-antigen and R-core are called "smooth," while molecules that have only R-core are called "rough." S-LPS refers to smooth LPS (e.g., containing O-antigen). R-LPS refers to rough LPS. The R-core is further subdivided, according to its length, from Ra (complete core) to Re (only 2-keto-3-deoxy-octulosonic acid (KDO)). The term "deep-rough" LPS refers to Re LPS. SR-LPS have one O-antigen repeat until attached to the R-core.

FIG. 4 shows binding of the putative enzyme to LPS. A preparation of partially purified enzyme was radiolabeled with $^{125}$I. The radiolabeled proteins were then incubated with or without LPS for 1 hour at 22° C. Staphylococci that had been coated with IgG antibodies to the LPS were then added, and after further incubation at 4° C. the staphylococci were washed extensively and then solubilized in SDS digestion buffer (2% SDS, 20% glycerol) and the $^{125}$I-labeled proteins that bound to the staphylococci were analyzed by SDS-polyacrylamide gel electrophoresis and autoradiography. The lane marked * contained the mixture of labeled proteins. Lanes 1 through 4 contained staphylococci that were incubated with the labeled proteins; LPS and anti-LPS antibody were included in the incubation mixtures as indicated. A single radiolabeled protein bound specifically to the staphylococci when both LPS and anti-LPS were included (lane 3). Nonradioactive molecular weight markers were included in the gel; the approximate size of the LPS-binding protein is indicated. This is the same band that is associated with enzymatic activity in all other purification steps.

DESCRIPTION OF THE PREFERRED EMBODIMENT

The present invention involves the use of a hydrolytic enzyme to detoxify bacterial lipopolysaccharide (LPS or endotoxin). This detoxification involves the hydrolysis of the ester bonds between nonhydroxylated acyl functions and the hydroxy groups of 3-hydroxymyristoyl (3-hydroxytetradecanoate) or other 3-hydroxy fatty acyl residues. These 3-hydroxymyristoyl functions are, in turn, bound in ester or amide linkage to a D-glucosaminyl disaccharide structure of the LPS lipid A moiety (see FIG. 2). The term acyloxyacyl hydrolase is used here to refer to this enzymatic activity.

An acyloxyacyl hydrolase was partially purified from cells of a human promyelocyte cell line, HL-60, and used to deacylate LPS from *S. typhimurium*. The enzymatically deacylated LPS lacked nonhydroxylated fatty acids but retained phosphate, 3-hydroxymyristoyl residues, and the polysaccharide chain. The effect of acyloxyacyl hydrolysis on the biological activities of the LPS was studied in several test systems. Loss of bioactivity in these assays was directly related to the degree of deacylation. Removal of approximately 95% of the non-hydroxylated fatty acids from the LPS had relatively minor impact on B-cell mitogenicity (5- to 12-fold loss of activity); intermediate effects on pyrogenicity and Limulus lysate clotting activity, (10- to 20-fold loss of activity); and major impact on preparing the skin for the dermal Shwartzman reaction and on the stimulation of human vascular endothelial cells (greater than 100-fold loss of activity). The tissue toxicity of the LPS, measured in the Shwartzman reaction, was thus reduced at least 10-fold more than the immunostimulatory activity, measured in the B-cell mitogenicity assay.

These results generally agree with the reported roles of acyloxyacyl groups in the bioactivities of lipid A analogs. The presence of the hydrophilic LPS polysaccharide thus does not appear to alter greatly the influence that acyloxyacyl residues have in the biological activities of lipid A.

The discoveries comprising the present invention include the first description of an enzymatic activity that modifies the bioactivities of LPS. Acyloxyacyl hydrolase activity has been found in human neutrophils and mouse macrophages; the latter cells also contain mechanisms for removing 3-hydroxymyristate residues from LPS. Antibody-opsonized LPS undergo deacylation by both neutrophils and macrophages, so acyloxyacyl hydrolases should act on the LPS in phagocytosed bacteria as well. In addition to *Salmonella* LPS, the enzyme also deacylates LPS from other bacteria (*E. coli, Hemophilus influenzae, Neisseria meningitidis*, for example, Acyloxyacyl hydrolases are most likely located in an acid intracellular compartment (lysosomes or endosomes), where deacylation of bacterial LPS would accompany the digestion of other bacterial components. Neutrophils are the front line of host defense against bacterial invasion, yet they are short-lived in tissue and also appear to regurgitate part of the material that they ingest; partially deacylated LPS, released from the neutrophils, may then interact with other host cells. It should be emphasized that the intracellular fate of LPS is not completely understood and that existing studies have all dealt with purified LPS, not the LPS in bacteria per se. Presently unknown deacylases, acyl transferases, or phosphatases may also process LPS intracellularly, with a variety of potential effects on LPS bioactivity.

It should also be noted that acyloxyacyl hydrolase activity has been found in the serum of rabbits, mice, and man (Munford, R. S., unpublished). Low levels of activity are present in normal mouse and rabbit serum; these levels can be increased 3- to 5-fold by immunization of rabbits with Gram-negative bacteria. The rabbit serum acyloxyacyl hydrolase activity has a somewhat higher pH optimum (5 to 6) than that found for human neutrophil acyloxyacyl hydrolase (4.5 to 5.0). Although normal human serum does not appear to have detectable acyloxyacyl hydrolase activity, low levels of activity have been found in the plasma of some patients with Gram-negative bacterial bloodstream infection. These preliminary studies suggest that animals respond to Gram-negative bacterial immunization or infection by increasing the acyloxyacyl hydrolase activity in their blood. Presumably the enzyme(s) in blood may either (1) bind to circulating LPS, targeting the LPS to be taken up by phagocytic cells, where acyloxyacyl hydrolysis would occur, or (2) act on LPS in local tissue sites of infection.

The major role of acyloxyacyl hydrolases in animals may be to prevent LPS tissue toxicity. Remarkably, acyloxyacyl hydrolysis has a much smaller negative impact on the immunostimulatory potency of LPS, at least as measured by assays such as B-cell mitogenicity. Preservation of the immunostimulatory activities of LPS would allow animals to derive benefits such as immune priming during health and the enhancement of antibody formation during infections. In this regard it is interesting to consider that acyloxyacyl hydrolases may have a role similar to lysozyme, another enzyme of phagocytic cells that cleaves a toxic bacterial cell wall polymer (peptidoglycan) into products (muramyl peptides) that have immunostimulatory activities.

The present invention comprises the identification, characterization and purification of a human acyloxyacyl hydrolase. This acyloxyacyl hydrolase hydrolyzes the ester bonds between the carboxyl functions of non-hydroxylated fatty acids and the 3-hydroxy functions of 3-hydroxy fatty acids bound in ester or amide linkages to glucosamine disaccharide of lipid A. The ester or amide bonds between LPS glycosaminyl residues and the carboxylate of the 3-hydroxy fatty acids appear entirely or at least substantially unaffected by acyloxyacyl hydrolase. Acyloxyacyl hydrolase action on LPS affects both LPS toxicity and LPS immunostimulatory activity. LPS toxic effects are more greatly reduced by hydrolytic release of non-hydroxylated fatty acids than are the LPS immunostimulatory effects.

Thus, the acyloxyacyl hydrolase may be administered as a therapeutic agent to patients subject to septic shock, for example, due to infection by Gram-negative bacteria. The administration of therapeutically effective amounts of the human acyloxyacyl hydrolase should decrease the toxicity of the bacterial LPS while not abolishing potentially helpful LPS biogenic effects such as B lymphocyte stimulation. A prophylactic use of this enzyme may be appropriate where septic shock is a distinct possibility. These uses may be by the usual modes of administration such as by injection into veins, arteries, or peritoneum. Whether administered therapeutically or prophylactically, exogenous acyloxyacyl hydrolase would supplement the patient's own capacity to produce the enzyme, increasing enzyme levels in blood and, possibly, in phagocytic cells.

The antigen structure of the polysaccharide regions of LPS is not altered by acyloxyacyl hydrolysis. Enzymatic detoxification of lipid A without destruction of immunostimulatory activity may thus produce non-toxic LPS vaccines; the adjuvanticity of the detoxified lipid A would help promote the formation of antibodies to the polysaccharide antigen(s). As noted above, such antibodies may protect animals from various Gram-negative bacterial diseases.

LPS that have been detoxified by acyloxyacyl hydrolase may also be used therapeutically to antagonize the toxic effects of LPS present in (or released from) infecting bacteria. Enzymically deacylated LPS inhibits the ability of native LPS to stimulate the expression by human endothelial cells of a neutrophil-adherence factor (Pohlman, Munford, and Harlan, J. Exp. Med., V 165, p 1393, 1987). Deacylated LPS were inhibitory when added as long as 60 min after the native LPS. The adherence of neutrophils to endothelial cells is thought to play a role in the toxic effects of LPS. In addition, a lipid A analog that structurally resembles the product of acyloxyacyl hydrolysis has been shown capable of reversing endotoxic shock in mice and sheep (Clin. Res., V 34, p 518A, 1986). n=toxified LPS may be superior to lipid A analogs for this purpose since the hydrophilic LPS polysaccharide chain enhances the solubility of the molecules in aqueous environments.

A further use of the enzyme may be to reduce the toxicity of therapeutic liquid injectants which may be contaminated with LPS. Adding acyloxyacyl hydrolase to the injectant and allowing the enzyme to enzymatically hydrolyze ester bonds should detoxify LPS contained therein.

The following examples are presented to illustrate preferred embodiments of aspects of the present invention but are not intended to limit the scope of the invention unless otherwise specifically so stated in the claims appended hereto.

EXAMPLE 1

Purification of Acyloxyacyl Hydrolase

Cell source. HL-60 cells (American Typ Collection, Rockville, Md., (ATCC) strain CCL-240) were propagated in RPMI-1640 medium that contained 8% fetal bovine serum (Hyclone), 10 units/ml penicillin G, and 50 ug/ml streptomycin. Typically, cultures of 250 ml in 750 ml flasks (Falcon) were harvested after 4–5 days of growth at 37° C. in an atmosphere of 5% $CO_2$. Twenty flasks (5L medium) yielded approximately $5 \times 10^9$ cells. The cells were collected by centrifugation (500×g, 10 min, 4° C.), washed once with PBS (10 mM sodium phosphate, 0.15M sodium chloride, pH 7.1), and resuspended in 10 ml relaxation buffer (100 mM KCl, 3 mM NaCl, 3.5 mM $MgCl_2$, and 10 mM HEPES, pH 7.4).

The cells were then disrupted using several strokes in a Dounce homogenizer, followed by centrifugation (478×g, 5 min, 4° C.) to pellet nuclei and unbroken cells. The pellet was resuspended in 10 ml relaxation buffer and the homogenization-centrifugation was repeated. This cycle was continued (usually 4-5 times) until only approximately 5-10% of the cells were unbroken, as judged by microscopic examination of the pellet. The pooled supernatants from $5 \times 10^9$ cells typically contained 800-1,000 mg protein.

Enzyme preparation. Granules containing the enzyme were sedimented by centrifugation at 20,000×g for 10 min at 4° C. The supernatant was recentifuged and the combined pellets were resuspended in 27 ml relaxation buffer. Triton X-100 was added (0.5% vol/vol) and after the suspension sat for 10 minutes in an ice bath, distilled water was added to bring the volume to 30 ml (Triton X-100, concentration of 0.05%). Phenylmethylsulfonylfluoride (PMSF) and pepstatin were added (5 mM and 1 nM, respectively), and the preparation was centrifuged at 100,000×g for 60 min at 4° C. The pellet was discarded and the supernatant was frozen at $-20°$ C. With the exception of hydroxyapatite chromatography and hydrophobic interaction chromatography, all purification steps were carried out at about 4° C.

Lentil lectin chromatography. After another addition of PMSF and peptstatin, the 100,000×g supernatant was diluted 2-fold in lectin column buffer (25 mM NaCl, 10 mM MES, pH 6.0, 0.01% Triton X-100) and applied to a (0.9 cm × 15 cm) column of lentil lectin-Sepharose 4B (Pharmacia). The column was washed sequentially with 15 ml volumes of 10 mM MES, pH 6.0, 0.01% Triton X-100, that contained (1) 0.025 M NaCl, (2) 0.15 M NaCl with 0.5 M alpha-methyl mannoside, and (3) 0.5 M NaCl with 0.5 M alpha-methyl mannoside. The entire protein peak that eluted from the column was collected and frozen at $-20°$ C.

Hydrophobic interaction chromatography. The glycoprotein eluate was diluted with 0.5 volumes of column buffer (0.2 M (NH 4 mM NaH 6 mM Na 0.04% sodium azide, pH 6.8) and applied to a column containing 4 to 8 ml Phenyl-Sepharose CL-4B. After application of the sample, the column was washed with column buffer until the $O.D._{280}$ of the eluate reached a low plateau. A linear gradient was then applied to the column, using column buffer and elution buffer (75% ethylene glycol, 1.5 mM $NaH_2PO_4$, 8.5 mM $Na_2HPO_4$, 4, 0.04% sodium azide, pH 7.2) in a ratio of one part column buffer to two parts elution buffer. Fractions (3 ml) were collected and monitored for enzyme activity and optical density at 280 nm ($O.D._{280}$). The enzyme eluted with the first half of the peak of $O.D._{280}$ absorbance. Appropriate fractions were pooled and stored at $-20°$ C.

Hydroxyapatite (HPT) chromatography. The fractions from the preceding step were diluted 3-fold with HPT buffer (0.02M sodium phosphate, pH 7.0, 0.04% sodium azide, 0.01% Triton X-100) and applied to a 1.0×4.0 cm column of hydroxyapatite (Biorad HPT). Proteins were eluted with a gradient from 0.02 to 0.4M sodium phosphate in the same buffer. The peak of enzymatic activity eluted at a phosphate concentration of 0.2M. Glycerol (30%, vol/vol) was added and the fractions that contained the enzyme were pooled and concentrated using a Centricon-30 centrifugation device (Amicon).

Figure 3:
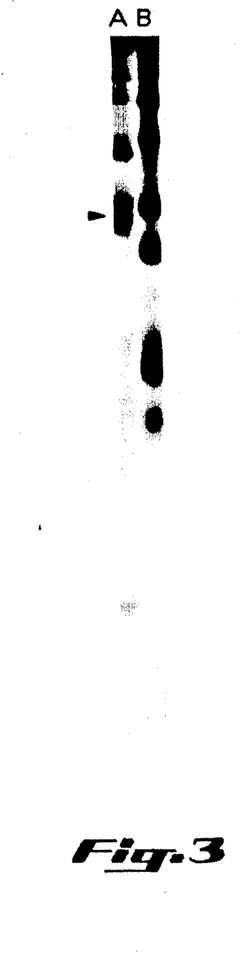
FIG. 3 shows an SDS-polyacrylamide gel analysis of purified enzyme. Lane A contains the enzyme preparation, purified more than 5,000-fold from the cell lysate. Lane B contains molecular weight markers. The gel was stained with silver. The arrow indicates the band that contains the enzyme, which in this 11% polyacrylamide gel has an approximate size of 70,000 to 75,000 Daltons. Each of the other bands is not present with the enzyme on one or more other analyses (size-exclusion chromatography, butylsepharose chromatography). The top two heavy bands in Lane A are recognized by a single monoclonal antibody and probably represent different forms of the same contaminating protein; this antibody adsorbs these proteins but not the enzymatic activity.
Figure 4:
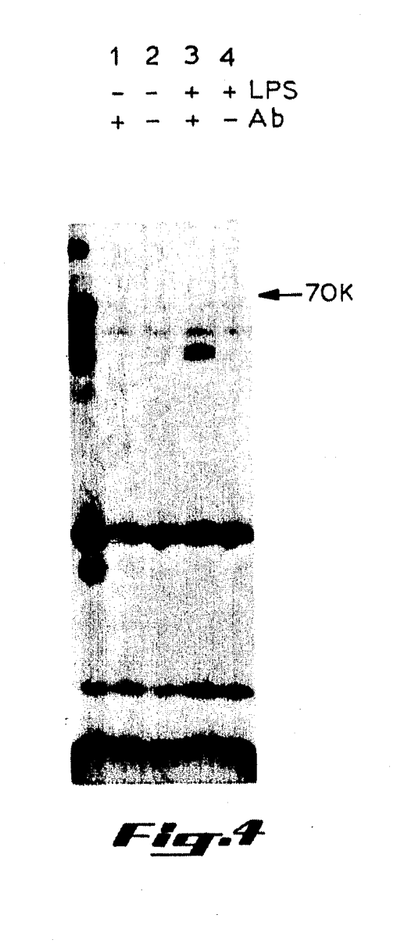

Cation exchange chromatography. The concentrated HPT fractions were diluted 10-fold in MonoS start buffer (0.15M sodium acetate, pH 4.5, 0.05% Triton X-100, 0.04% sodium azide, 2% taurine, 5% 2-propanol), centrifuged to remove particulates, and applied through a 0.22 micron filter to a MonoS column (Pharmacia). Using the FPLC system (Pharmacia), proteins were eluted from the column using MonoS start buffer with a gradient of 0-1.0 M NaCl. The peak of enzymatic activity eluted at a NaCl concentration of approximately 0.27-0.3M. Glycerol (28% vol/vol) was added to the peak fractions before they were pooled and concentrated as described above. The specific activity of the enzyme(s) in the MonoS peak fractions was at least 5,000-fold higher than in the post-nuclear homogenate. The protein composition of the final preparation was analyzed by polyacrylamide gel electrophoresis using sodium dodecyl sulfate; when stained with silver, the material showed at least 5 bands, including a prominent band at an apparent molecular weight of 70,000 to 75,000 Daltons (FIG. 3). As shown in FIG. 4, a protein of the same molecular weight was shown to bind to LPS, the for the enzyme.

A summary of the purification procedure is provided in Table 1.

TABLE 1

PURIFICATION OF ACYLOXYACYL HYDROLASE FROM HL-60 CELLS

| Procedure | Recovery (cumulative %) | | Specific activity (approximate) |
| --- | --- | --- | --- |
| | Protein | Enzyme activity | Activity/ug protein |
| Post-nuclear lysate | 100 | 100 | 1 |
| Triton X-100 soluble, 100,000 × g supernate of granule fraction | 5.8 | 75 | 13 |
| Lentil lectin (mannoside-elutable fraction) | 0.6 | 43 | 78 |
| Phenyl-Sepharose (ethylene glycol-elutable fraction) | 0.04 | 27 | 600 |
| Hydroxylapatite peak | 0.008 | 21 | 2500 |
| MonoS (FPLC cation exchange) peak | (?) 0.0001* | 13 | (?) 7500* |

*ACTUAL PROTEIN CONCENTRATION NOT MEASURED.

Alternative cell source. The above methods have also been used to purify acyloxyacyl hydrolase from human peripheral blood neutrophils. The properties of the enzymatic activity obtained from the two sources are essentially identical. Because it may be more readily obtained in larger quantities, the HL-60 cell enzyme has been used for the studies described in examples 2, 3, and 4.

EXAMPLE 2

Acyloxyacyl Hydrolase Activity Upon LPS

Incubation conditions. Biosynthetically radiolabeled LPS were prepared from *Salmonella typhimurium* grown in the presence of $^3$H-acetate and N-acetyl-1-[$^{14}$C]-glucosamine (incorporated into fatty acids and the glucosamine backbone, respectively, of the lipid A region). Acyloxyacyl hydrolysis was followed by measuring the release of $^3$H-fatty acids from the $^{14}$C-glucosamine-labeled LPS backbone.

Double-labeled quantities of $^3$H/$^{14}$C) LPS (5 ug) were incubated at 37° C. with purified enzyme (10 ul) in a reaction mixture (0.5 ml) that contained 1 mg/ml fatty acid-free bovine serum albumin (BSA) (Sigma), St. Louis Mo.), 5 mM $CaCl_2$, 0.5% (vol/vol) Triton X-100, and 20 mM Tris-citrate, pH 4.8. The reaction was stopped at the desired time points by precipitating the LPS and BSA with 1.2 ml 95% ethanol. The precipitate was collected by centrifugation (12,000×g, 10 min, 4° C.) and washed once with 1.0 ml 80% ethanol. The precipitates were suspended in 0.5 ml normal saline and stored at −20° C. Aliquots of the precipitates and supernatants were counted and the percentage of each radiolabel that appeared in the supernatant was calculated. $^{32}$P-labeled *S. typhimurium* Rc LPS, prepared by growing strain PRX20 in a low phosphate medium that contained $^{32}PO_4$ (orthophosphate, New England Nuclear, Boston, Mass.), were incubated in parallel and precipitated in the same way; $^{32}PO_4$, when incubated in parallel and processed identically, was completely recovered in the ethanol supernatant.

Fatty Acid Analysis. LPS were deacylated and precipitated with ethanol, and the ethanol-water supernatant was dried under $N_2$. The $^3$H-fatty acids were extracted into chloroform/methanol (2/1). Unincubated LPS and the deacylated LPS in the ethanol precipitate were hydrolyzed and the liberated fatty acids were extracted into chloroform. Recovery of radioactivity at each step was greater than 85%. The samples were analyzed by one-dimensional TLC using Silica gel G plates (Analtech). The solvent system was petroleum ether/diethyl ether/acetic acid (70/30/1). The spots were scraped from the plate and radioactivity measured (84–96% recovery of added radioactivity). Values reported are the means of duplicate determinations.

Figure 5:
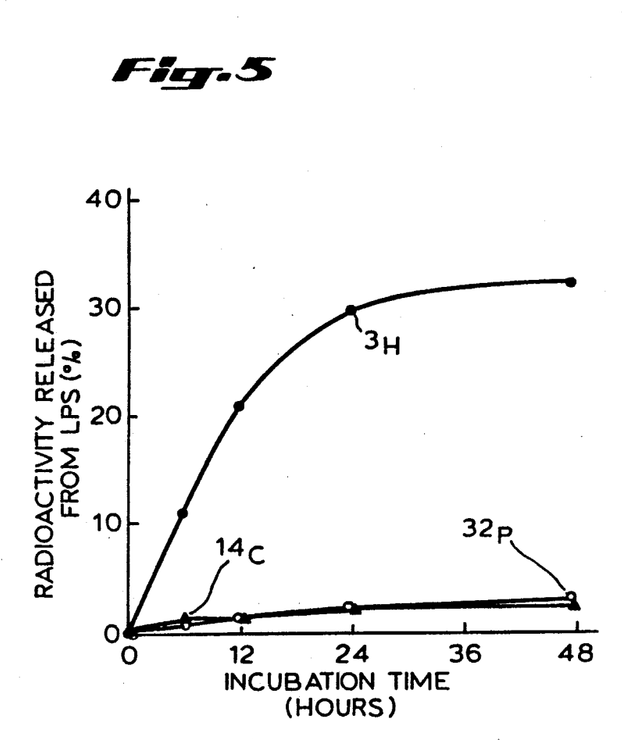
FIG. 5 shows the time course for release of $^3$H-fatty acid, $^{14}$C-glucosamine and $^{32}$P-phosphate from labeled LPS in the presence of acyloxyacyl hydrolase.

Deacylation of LPS. The time course of the deacylation reaction is shown in FIG. 5. $^3$H-fatty acids were released from the LPS over time, while neither $^{14}$C nor $^{32}$P (present in $^{32}$P-labeled *S. typhimurium* LPS that was treated with enzyme in parallel with the $^3$H/$^{14}$C LPS) was released significantly. The reaction reached an apparent maximum when approximately 32% of the $^3$H-fatty acids were extracted from the LPS; since 35% of the $^3$H-counts in this preparation were in nonhydroxylated fatty acids (NFA), 32% deacylation was consistent with nearly complete removal of these residues. This conclusion was supported by analysis of the fatty acid composition of the substrate LPS and the reaction products; 65% of the $^3$H-fatty acid counts in the LPS were in 3-OH-14:0 and 35% were in NFA, whereas the deacylated fatty acids that were released from LPS were almost entirely (94%) nonhydroxylated and 95% of the fatty acids in the partially deacylated LPS were 3-OH-14:0.

Figure 6:
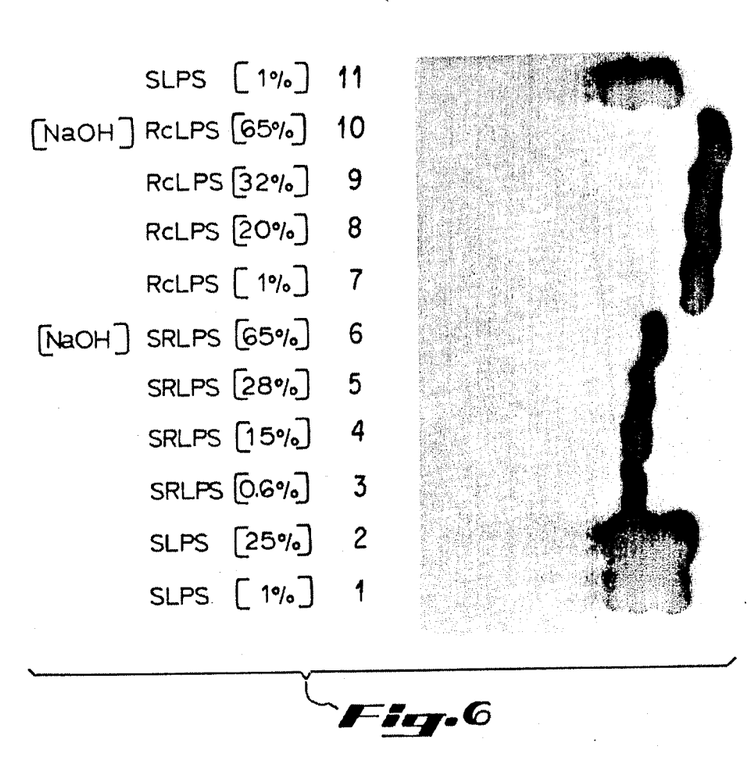
FIG. 6 shows the effects of deacylation upon labeled LPS samples subjected to electrophoresis in polyacrylamide gel with sodium dodecyl sulfate. Each lane contained 0.5 ug LPS. The gel was treated with En$^3$Hance (New England Nuclear) and exposed to Kodak X-Omat XAR-5 film at −70° C. Lane 1 contained S-LPS (about 1% deacylated); lane 2, S-LPS (25% deacylated); lane 3, SR-LPS (0.6% deacylated); lane 4, SR-LPS (15%); lane 5, SR-LPS (28%); lane 6, SR-LPS (65% deacylated with NaOH); lane 7, Rc-LPS (1%); lane 8, Rc-LPS (20%); lane 9, Rc-LPS (32%); lane 10, Rc-LPS (65% deacylated with NaOH); and lane 11, S-LPS (1%). The LPS in lanes 6 and 10 were deacylated by treatment with NaOH, which hydolyzed all ester bonds.

As shown in FIG. 6, samples of acylated and deacylated LPS were solubilized in sample buffer and subjected to electrophoresis in polyacrylamide gel with sodium dodecyl sulfate (SDS-PAGE).

Enzymatic deacylation produced an increase in the migration of the LPS in SDS-PAGE, consistent with a reduction in the size of the molecules (FIG. 6). This increase in migration was less than was observed for LPS that had been treated with alkali, which removes all four of the ester-linked fatty acids from lipid A (compare lanes 5 and 6, 9 and 10). Preservation of the original ladder pattern (which reflected the presence of molecules with different numbers of 0-repeat units in the deacylated smooth LPS (lanes 1 and 2) indicated that the polysaccharide chain was not removed by enzymatic treatment.

Taken together, the evidence shows that the only modification in the enzymatically treated molecules was the loss of NFA.

EXAMPLE 3

Characteristics of Acyloxyacyl Hydrolase from Human Neutrophils

Enzymatic activity was approximately 5,000 fold increased in the MonoS peak fraction relative to the post-nuclear homogenate. The enzymatic activity was abolished by heating for 10 min at 80° C. but was not inhibited by EDTA (10 mM), PMSF (5 mM), pepstatin (1 mM), para-hydroxymercuribenzoate (0.2 mM), sodium fluoride (50 mM), TPCK (0.1 mM), TLCK (0.1 mM), or soybean trypsin inhibitor (10 ug/ml). Calcium chloride (5–10 mM) and Triton X-100 (0.5% vol/vol) were required for maximal activity. Sodium deoxycholate inhibited the reaction. On gel filtration chromatography, the enzymatic activity eluted as a single peak with an approximate size of 50,000 to 70,000 Daltons. The prior exposure of the preparation to Triton X-100 may artifactually influence this molecular weight estimate. To identify the molecular weight of the enzyme more precisely, maximally pure preparations (containing approximately 5 protein bands on silver-stained SDS-polyacrylamide electrophoresis gels as shown in FIG. 3) were radioiodinated and subjected to additional analyses. When the radioiodinated mixture was incubated with LPS, and the LPS was then adsorbed from solution using solid-phase anti-LPS antibodies, a single radioactive protein was found to bind to the LPS. This band had an apparent molecular weight on SDS-PAGE (11% polyacrylamide) of approximately 70,000 to 75,000 Daltons (FIG. 4); the same radioactive band co-eluted with enzymatic activity and had an apparent size of 50,000–70,000 on size exclusion chromatography (Superose 12, Pharmacia Labs., Inc., Piscataway, New Jersey). The discrepancy in apparent molecular size may reflect the degree of glycosylation of the enzyme and its retardation on certain column supports. Indeed, the apparent molecular weight of the protein increases as the percentage of polyacrylamide in the electrophoresis gels is increased, again consistent with the behavior of a glycoprotein.

Figure 7:
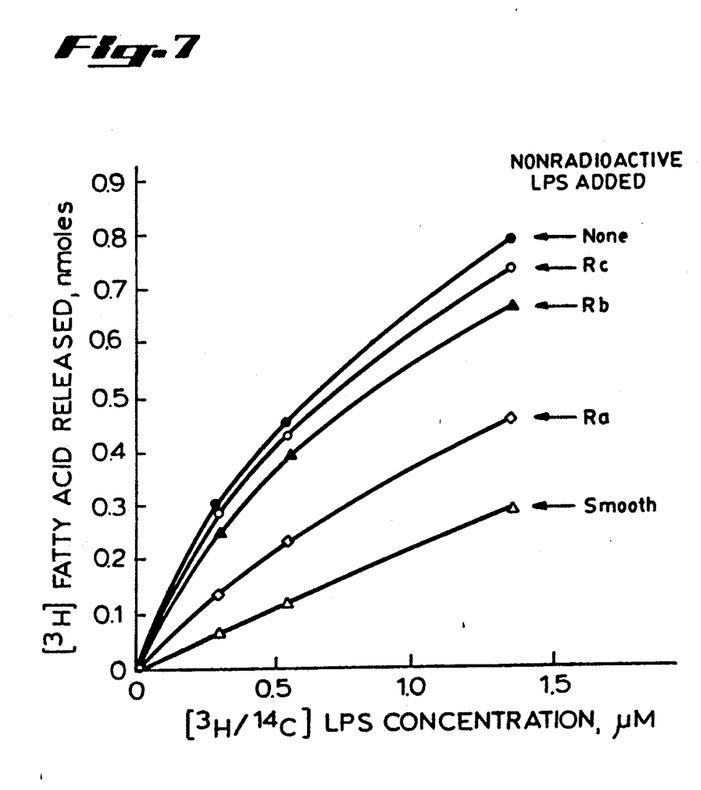
FIG. 7 shows the ability of nonradioactive LPS to diminish the release of $^3$H-fatty acids from the radiolabeled LPS substrate. Nonradioactive LPS from *S. minnesota* were added (adjusted to 0.27 umoles) to reaction mixtures that contained 0.27 umoles radiolabeled Rc-LPS. After incubation at 37° C. for 9 hours, the amount of released $^3$H-fatty acid was determined by extracting the fatty acids into chloroform and counting. The nonradioactive LPS had approximately 6 (Rc), 9 (Rb), 10 (Ra), and 14–50 (smooth) saccharides attached to lipid A.

Nonradioactive LPS will compete with the radiolabeled LPS substrate. The longer the polysaccharide chain in the nonradioactive LPS, the better the competition (FIG. 7). When LPS with different polysaccharide chain lengths were radiolabeled and used as substrates for the enzyme, the shortest-chain LPS (Rc) underwent significantly less hydrolysis than did the longer-chain LPS. Thus acyloxyacyl hydrolase was more active in vitro on LPS substrates with long polysaccharide chains.

To test the ability of the purified enzyme to deacylate LPS from different than negative bacteria, radiolabeled LPS were prepared from S. typhimurium and E. coli (2 members of the family Enterobacteriaceae), and from 2 distantly related species, Neisseria meningitidis (family Neisseriaceae) and Hemophilus influenzae (family Brucellaceae). In each instance, the enzyme preferentially removed the non-hydroxylated fatty acids from the LPS. Since acyloxyacyl acyloxy linkages have been found in the LPS from all medically important Gram negative bacteria studied, it is likely that susceptibility of LPS to acyloxyacyl hydrolyase is a general phenomenon.

The purified enzyme did not contain measurable amounts of phosphatases acting to dephosphorylate either S. typhimurium Rc LPS or deep-rough E. coli LPS. The absence of such phosphatase activity is preferred for practices of the present invention.

A series of samples that contained increasing amounts of acyloxyacyl hydrolase activity was found to have decreasing amounts of hydrolytic activity toward methylumbiliferyl oleate, a substrate for the enzyme, acid lipase. Additionally, it was found that acyloxyacyl hydrolase did not show hydrolytic activity toward cholesterol esters, glycerol trioleate, or toward dipalmitoylphosphatidylcholine, further distinguishing acyloxyacyl hydrolase from more common hydrolytic enzymes.

EXAMPLE 4

Alteration by Acyloxyacyl Hydrolase of LPS Bioactivities

R-LPS (rough LPS with short polysaccharide chain) from S. typhimurium was treated with acyloxyacyl hydrolase purified as described herein.

The deacylation of LPS was performed by incubating constant amounts of R-LPS and acyloxyacyl hydrolase for different time periods to produce different degrees of deacylation. Background deacylation (LPS incubated without enzyme) of 0.5–2.2% was subtracted from each value. Controls in each bioactivity assay included the reaction mixture and the reaction mixture that contained enzyme but no LPS; these controls were always negative.

The effects of acyloxyacyl hydrolysis on the bioactivities of the LPS were examined in six assays. The dermal Shwartzman reaction and the rabbit pyrogen test were used to measure in vivo toxicity. The mouse spleen cell (B-lymphocyte) mitogenicity assay, the stimulation of murine macrophages to release prostaglandins, and the stimulation of human vascular endothelial cells to express neutrophil-adherence factor were used to measure in vitro bioactivities of LPS.

A dermal Shwartzman reaction was performed by intradermal injection of 2.5 ug of LPS or enzymically deacylated LPS into New Zealand white rabbits. Twenty-two hours later, the animals were given an intravenous dose of R-LPS (2–4ug/kg). The dermal lesions were scored 4 or 6 hours later by 2 persons not knowing the identity of the samples. The average results from two rabbits are presented in the second and third columns of table 1.

Thermal response index (TRI) for LPS preparations was determined by injecting a New Zealand white rabbit weighing 3–4 kg with an intravenous dose of 50 ng LPS. Temperature was monitored with a rectal probe and recorded every 10 min. The Thermal Response Index is the integrated product of the temperature above baseline (° C.) and time (degree-hours). (Zimmer et al. (1981) Peptides, V 2, p 413) Each dose was tested in 3 or 4 rabbits.

B-cell proliferation was measured by first incubating LPS preparations with murine splenocytes in 98-well microtiter plates as described by Wannemuehler et al. (1984) J. Immunol. V 133, p 299. After 24 hours, methyl-[$^3$H]thymidine (0.5 uCi) was added to each well. The amount of radioactivity incorporated into each cell culture was measured 18 hours later. Each LPS was tested in four 5-fold dilutions; probit analysis of the results indicated the amount of each preparation that produced half-maximal stimulation of B-cell proliferation. The maximal stimulation index ($^3$H-radioactivity in stimulated cells / $^3$H-radioactivity in unstimulated cells) in the two experiments shown in Table 2 was 30 and 29, respectively.

The fourth assay was the Limulus lysate test, an in vitro clotting assay for LPS. Limulus lysate clotting was measured using 50 ul lysate (Cape Cod Associates, Woods Hole, Mass.) that contained 0.8 mg/ml n-benzoyl-L-valylglycyl-L-arginine PNA (Vega Biochemicals, Tucson, AZ) and 50 ul test sample. After incubation for 55 min at 37° C., 0.7 ml 40% acetic acid was added to each tube and the absorbance at 405 nm was measured. The values shown were derived by applying the results of 10-fold dilutions of test samples to a standard curve that was constructed with Rc LPS, with normalization to a starting concentration of 10 ug/ml. Dilutions were performed in pyrogen-free water. Each value is the mean of duplicate determinations that differed by less than 10%. Similar results were obtained in two additional experiments.

The stimulation of murine macrophages to release prostaglandin $E_2$ was also used as an index of immunostimulatory activity. Thioglycolate-elicited C3H/HeN mouse macrophages were incubated with acylated and 29%-deacylated LPS for 40 hours at 37° C. as described by Munford and Hall (1985) Infection and Immunity, V 48, pp. 464–473. PGE$_2$ levels in the cell supernatants were measured by radioimmunoassay (Campbell et al. (1980) Hypertension, V 2, pp 472–476).

LPS stimulates vascular endothelial cells to express cell-surface factor(s) that promote the adherence of neutrophils to the endothelial cell surface. This activity is thought to play a role in the toxicity of LPS as well as in the attraction of neutrophils to tissue sites of bacterial infection. In collaborative studies, the ability of LPS and deacylated LPS to stimulate the adherence of $^{51}$Cr-labeled human neutrophils to monolayers of human umbilical vein endothelial cells was tested (Pohlman et al. (1987), J. Exp. Med., V 165, p 1393).

The effects of acyloxyacyl hydrolysis on the bioactivities of LPS in these assays were studied in two ways. First, the impact of maximal LPS deacylation (30–32% loss of $^3$H-fatty acids) was assessed in each bioassay. Second, the dose-response relationship (degree of deacylation vs. loss of bioactivity) was studied in three of the assays.

Impact of Maximal Deacylation. An intradermal injection of LPS, when followed 20 to 24 hours later by an intravenous injection of LPS, produces hemorrhagic necrosis of the skin at the intradermal injection site (dermal Shwartzman reaction). Maximally deacylated LPS (32% loss of $^3$H-fatty acids) did not prepare the skin for the reaction at doses as high as 10 ug, whereas LPS that had been incubated in reaction mixture without enzyme produced hemorrhage (4–5 mm diameter) and induration at doses of 0.1 ug; the reduction in toxicity was thus 100-fold or greater. Determination of the actual end-point was precluded by the lack of sufficient enzyme to deacylate the required large amounts of LPS. Deacylated LPS were also substantially less pyrogenic in rabbits than fully acylated LPS. Intravenous doses of 62 ng/kg of acylated and 32%-deacylated LPS produced mean thermal response indices of 12.0±2.5 (S.D.) and 5.0±1.0, respectively, while the indices with 25 ng/kg doses were 8.5±1.9 and 2.8±1.1, respectively. Deacylation of 32% of the $^3$H-fatty acids was associated with approximately 100- to 500- fold loss of stimulatory potency toward human umbilical vein endothelial cells, 20-fold loss of activity in the Limulus test, a 5- to 12-fold reduction in B-cell mitogenicity, and a 10- to 20-fold reduction in the release of PGE$_2$ by thioglycolate-elicited murine macrophages. Taken together, these results indicated that maximally deacylated LPS were at least 10-fold less toxic (as measured in the dermal Shwartzman test) than they were immunostimulatory (as measured by the B-cell mitogenicity test).

Dose-response. Table 2 shows the relationship between the degree of deacylation and the loss of bioactivity for three of the assays. In each assay, loss of activity was directly related to the degree of deacylation.

In summary, acyloxyacyl hydrolysis greatly reduced the tissue toxicity of LPS while preserving relatively more of the immunostimulatory activity. This conclusion was consistent with the results of experiments, discussed in Background, that used lipid A analogs to evaluate the stimulatory role of acyloxyacyl groups. Acyloxyacyl hydrolysis makes possible the detoxification of LPS from many different bacteria, including LPS with long polysaccharide chains. The reduction in bioactivity was directly related to the degree of deacylation (Table 1).

Changes may be made in the construction, operation and arrangement of the various elements, steps and procedures described herein without departing from the concept and scope of the invention as defined in the following claims.

TABLE 2
EFFECTS OF DEACYLATION ON LPS BIOACTIVITIES

| Deacylation of LPS[1] (%) | Dermal Shwartzman Reaction[2] (0-4+) | | Dose for half-maximal B-cell Proliferation[3] (ug/ml) | | Limulus lysate Activity[4] (ug/ml) |
|---|---|---|---|---|---|
| | Rabbit 1 | Rabbit 2 | Expt 1 | Expt 2 | |
| 0 | 3+ | 3+ | 0.024 | 0.016 | 6.7 |
| 11–15 | 4+ | 2+ | 0.055 | 0.08 | 4.6 |
| 20–22 | 2+ | 2+ | 0.087 | NT | 3.4 |
| 29 | 1+ | 0 | 0.100 | NT | 1.3 |
| 32 | 0 | 0 | 0.14 | 0.18 | 0.4 |

[1]($^3$H-fatty acids released/total $^3$H-fatty acids in LPS) × 100.
[2]Constant amounts (2.5 ug) of R-LPS that had undergone different degrees of deacylation were injected intradermally in New Zealand White rabbits. 0 = no reaction; 1+ = less than or equal to 4 mm hemorrage; 2+ = 5–9 mm hemmorhage; 3+ = 10–15 mm hemorrhage; 4+ = greater than 15 mm hemorrhage.
[3]Single-cell suspensions of C3H/HeN mouse spleen were incubated with LPS in 96-well microtiter plates and incorporation of $^3$H methyl thymidine measured.
[4]Limulus lysate clotting was measured using 50 ul lysate that contained 0.8 mg/ml n-benzoyl-L-valyl-glycyl-L-arginine PNA and 50 ul test sample.

What is claimed is:

1. A method of treating a mammal with Gram-negative bacterial septic shock or prophylactically treating said mammal susceptible to Gram-negative bacterial septic shock, the method comprising administering intravascularly to said mammal an amount of immunogenically tolerated acyloxyacyl hydrolase effective to prevent LPS tissue toxicity.

2. The method of claim 1 wherein the acyloxyacyl hydrolase is from serum, human peripheral neutrophils or human promyelocyte cell line HL-60.

3. The method of claim 1 wherein the acyloxyacyl hydrolase is from the human promyelocyte cell line HL-60.

4. The method of claim 1 wherein the acyloxyacyl hydrolase has a molecular weight as determined by gel exclusion chromatography of between about 50,000 Daltons and about 70,000 Daltons.

5. The method of claim 1 wherein the acyloxyacyl hydrolase is essentially devoid of hydrolytic activity toward cholesterol esters, glycerol tryoleate, dispalmitoylphosphatidylcholine and phosphoryl groups of lipopolysaccharide.

6. The method of claim 1 wherein the acyloxyacyl hydrolase has a molecular weight as determined by 11% polyacrylamide gel electrophoresis with sodium dodecylsulfate of between about 70,000 Daltons and about 75,000 Daltons.

* * * * *

UNITED STATES PATENT AND TRADEMARK OFFICE
CERTIFICATE OF CORRECTION

PATENT NO. : 5,200,184
DATED : April 6, 1993
INVENTOR(S) : Robert S. Munford et al It is certified that error appears in the above-indentified patent and that said Letters Patent is hereby corrected as shown below:

Column 14, claim 5, lines 43-44, replace the words "tryoleate dispalmitoylphosphatidylcholine" with —trioleate, dipalmitoylphosphatidylcholine—.

Signed and Sealed this

Twenty-fifth Day of January, 1994

Attest:

BRUCE LEHMAN

Attesting Officer    Commissioner of Patents and Trademarks